United States Patent
Chana et al.

(10) Patent No.: US 11,307,189 B2
(45) Date of Patent: Apr. 19, 2022

(54) METHOD AND PROBE APPARATUS FOR TESTING PHARMACEUTICAL PRODUCTS

(71) Applicant: Oxford University Innovation Limited, Oxford (GB)

(72) Inventors: Kamaljit Singh Chana, Oxford (GB); Saranjit Sihra, Hornchurch (GB); Pavinder Sagoo, Ilford (GB); Maxwell Adams, Oxford (GB); Vikram Sridhar, Oxford (GB)

(73) Assignee: OXFORD UNIVERSITY INNOVATION LIMITED

( * ) Notice: Subject to any disclaimer, the term of this patent is extended or adjusted under 35 U.S.C. 154(b) by 11 days.

(21) Appl. No.: 16/651,368

(22) PCT Filed: Sep. 28, 2018

(86) PCT No.: PCT/GB2018/052780
§ 371 (c)(1),
(2) Date: Mar. 27, 2020

(87) PCT Pub. No.: WO2019/064018
PCT Pub. Date: Apr. 4, 2019

(65) Prior Publication Data
US 2020/0264150 A1 Aug. 20, 2020

(30) Foreign Application Priority Data
Sep. 29, 2017 (GB) .................................... 1715860

(51) Int. Cl.
*G01N 25/00* (2006.01)
*G01K 17/00* (2006.01)
(Continued)

(52) U.S. Cl.
CPC ............. *G01N 33/15* (2013.01); *G01N 25/18* (2013.01); *G01N 27/18* (2013.01)

(58) Field of Classification Search
USPC ................................ 374/43, 45, 183, 141, 29
See application file for complete search history.

(56) References Cited

U.S. PATENT DOCUMENTS

2006/0282223 A1* 12/2006 Lewis .................... G01N 33/15
702/19
2016/0018264 A1  1/2016 Bowers et al.
(Continued)

FOREIGN PATENT DOCUMENTS

WO       90/13812 A1    11/1990
WO    2009/019698 A2     2/2009
(Continued)

OTHER PUBLICATIONS

International Search Report and Written Opinion for PCT/GB2018/052780, dated Feb. 18, 2019, pp. 1-15.
(Continued)

*Primary Examiner* — Mirellys Jagan
(74) *Attorney, Agent, or Firm* — Thomas | Horstemeyer, LLP

(57) ABSTRACT

A sensor element (4) is used to apply a heating pulse to a pharmaceutical product (6). Chemical or structural information about the pharmaceutical product is determined by measuring a response of the sensor element (4) during the heating pulse. The response is dependent on a heat transfer characteristic of the pharmaceutical product (6).

14 Claims, 14 Drawing Sheets

(51) Int. Cl.
    *G01K 1/00*            (2006.01)
    *G01K 7/00*            (2006.01)
    *G01N 33/15*           (2006.01)
    *G01N 25/18*           (2006.01)
    *G01N 27/18*           (2006.01)

(56)                  References Cited

U.S. PATENT DOCUMENTS

2016/0077091 A1*    3/2016    Tyrrell ............ G01N 33/48792
                                                                       436/501
2016/0290849 A1     10/2016    Badarlis et al.
2016/0370340 A1*    12/2016    Blackley ............ G01N 33/0004

FOREIGN PATENT DOCUMENTS

WO        2010/089744 A1     8/2010
WO        2016/097723 A1     6/2016

OTHER PUBLICATIONS

UK Search Report for GB 1715860.1, dated Mar. 14, 2018, pp. 1-5.
UK Search Report for GB 1715860.1, dated Sep. 21, 2018, pp. 1-2.
Price et al., "Micro-thermal analysis: scanning thermal microscopy and localised thermal analysis", International Journal of Pharmaceuticals, Elsevier, NL, vol. 192, No. 1, Nov. 19, 1999, pp. 85-96.
International Preliminary Report on Patentability for PCT/GB2018/052780, dated Mar. 31, 2020, pp. 1-9.

* cited by examiner

METHOD AND PROBE APPARATUS FOR TESTING PHARMACEUTICAL PRODUCTS

CROSS-REFERENCE TO RELATED APPLICATIONS

This application is the National Stage of International Application No. PCT/GB2018/052780, filed Sep. 28, 2018, which claims priority to GB 1715860.1, filed Sep. 29, 2017, which are entirely incorporated herein by reference.

BACKGROUND

The present invention relates to sensing, particularly of pharmaceutical products such as tablets, particularly for detecting counterfeit medication, for quality control in a manufacturing facility, or for monitoring correct administration of medicines to patients.

The World Health Organisation currently estimates that between 5-8% of total pharmaceutical trade is carried out with counterfeit medication. In 2009 more than 72,000 boxes of counterfeit medication were bought directly by the NHS in the UK and put into circulation.

Currently a suspected drug would have its package analysed visually to see whether it is a fake. Counterfeit manufacturers are making that job much more difficult. Chemical checks are more reliable but can be costly and time consuming. Chemical checking may not be practical at the point of sale.

Stringent quality control standards need to be met during manufacture of medicines. Chemical testing of batches is costly. Furthermore, it can be difficult to detect variations in quality early enough to prevent significant amounts of sub-standard product being produced before corrective action is taken to restore product quality.

It is an object of the invention to at least partially address one or more of the above problems.

SUMMARY

According to an aspect, there is provided a method of sensing a pharmaceutical product, comprising: using a sensor element to apply a heating pulse to the pharmaceutical product; and determining chemical or structural information about the pharmaceutical product by measuring a response of the sensor element during the heating pulse, the response being dependent on a heat transfer characteristic of the pharmaceutical product.

Thus, a method is provided that allows the authenticity and/or a level of quality of a pharmaceutical product to be tested rapidly, using inexpensive, safe, and compact equipment. The method is non-destructive and highly sensitive.

In an embodiment, the information about the pharmaceutical product is at least partially obtained from a combination of a first measured response to a heating pulse and a second measured response to a heating pulse. An average temperature of the region being sensed during obtaining of the first measured response is different from an average temperature of the region being sensed during obtaining of the second measured response. This approach allows more detailed information to be obtained about physical characteristics of the product being tested. In particular, it is possible to obtain information about the density of the pharmaceutical product. A malicious party trying to fabricate fake versions of a pharmaceutical product would now need to ensure that the fake product not only has very similar heat transfer characteristics (e.g. a similar thermal product), but also very similar density. This requirement significantly increases the difficulties and costs for the malicious party.

In an embodiment, the sensor element comprises a resistive element. In an embodiment the resistive element is a thin film resistive element, optionally comprising platinum or gold. Thin film resistive elements are naturally compact. When provided flat against a substrate the thin film element is robust mechanically, and can easily be protected by a thermally conductive protective layer, such as a layer of diamond-like carbon.

In an embodiment the resistive element is mounted on a substrate in such a way that at least 10% of the surface area of the resistive element is in contact with the substrate (e.g. as a thin film element mounted on a substrate). An advantage of this arrangement is that significant heating power can be applied to the resistive element without the resistive element reaching excessively high temperatures. The substrate acts to conduct heat effectively away from the resistive element.

In an embodiment, heat from the heating pulse propagates through plural layers of different chemical or structural composition and the measured response of the sensor element is analysed to identify one or more target time periods, each target time period being defined as a time period in which the response of the sensor element is determined predominantly by a different combination of one or more of the plural layers. Information about particular target layers in a multilayer structure can therefore be obtained. Perfect contact between the sensor element and the pharmaceutical product to be sensed is not necessary because a contribution to the response of the sensor element from material between the sensor element and the pharmaceutical product (in the case of imperfect contact) can be recognized and taken account of. In an embodiment, a coupling fluid or gel is provided between the sensor element and the pharmaceutical product during application of the heating pulse to the pharmaceutical product. The coupling fluid or gel helps reproducibly to provide a high quality thermal contact between the sensor element and the region being sensed.

According to an aspect, there is provided a probe apparatus, comprising: a sensor element configured to be brought into thermal contact with a pharmaceutical product to be sensed; a measurement unit configured to apply a heating pulse to the pharmaceutical product via the sensor element and measure a response of the sensor element during the heating pulse, the response being dependent on a heat transfer characteristic of the pharmaceutical product; and a data processing unit configured to compare the measured response or chemical or structural information determined from the measured response with a stored reference response obtained at a previous time from a reference pharmaceutical product or with stored chemical or structural information about the reference pharmaceutical product.

In an embodiment, the sensor element is provided at the distal end of a probe, the probe having a handle and being configured such that a user can bring the sensor element into thermal contact with a pharmaceutical product to be sensed while holding the probe by the handle. The probe apparatus may comprise a deformable coupling member configured to deform on engagement with the pharmaceutical product when the probe is brought into contact with the pharmaceutical product, wherein the sensor element is mounted on, in, and/or in thermal contact with, the deformable coupling member. Thus, a probe apparatus is provided which can be manipulated easily by a user. The deformation of the deformable coupling member makes it easier for a user to repeatably bring the sensor element into thermal contact with pharmaceutical products to be sensed with a minimum variation in a quality of the thermal contact from one instance of the sensing to another instance of the sensing. The deformation reduces variation in a force of engagement between the sensor element and the product to be sensed relative to the alternative case where the sensor element is mounted on a rigid element. The deformable coupling member may allow a surface of engagement of the probe apparatus to conform with a surface of the product to be sensed during measurement.

In an embodiment, the probe apparatus comprises a receptacle configured to receive the pharmaceutical product and wherein the sensor element is configured to engage against the pharmaceutical product when the pharmaceutical product is located within the receptacle. The provision of a receptacle makes the probe apparatus easier to use and/or provides more repeatable measurement results. In an embodiment, multiple receptacles are provided, allowing multiple measurements to be made simultaneously. This may allow many instances of the same product to be sensed, thereby improving accuracy by averaging and/or providing information about product variation within a batch. Alternatively or additionally, the multiple receptacles may be used to quickly and efficiently compare a product of interest (e.g. a suspected fake product or a product in a batch that is being tested for quality) with a reference product (e.g. a known real product or a product known to have an acceptable level of quality).

In an embodiment, the probe apparatus further comprises a deformable coupling member configured to deform on engagement with the pharmaceutical product when the pharmaceutical product is in the receptacle, wherein the sensor element is mounted on, in, and/or in thermal contact with, the deformable coupling member. The deformable coupling member helps to ensure that good thermal contact is repeatably achieved between the product to be tested and the sensor element.

In an embodiment, the sensor element and associated electrical connections are printed onto a flexible film which is brought into contact with the product to be sensed by pulling the film onto the product using a vacuum packing technique.

According to an aspect, there is provided a storage device for a pharmaceutical product, the storage device comprising: a receptacle configured to receive a pharmaceutical product; and a measurement unit configured to apply a heating pulse directly or indirectly to an interior of the receptacle via a sensor element and measure a response of the sensor element during the heating pulse, the response being dependent on a heat transfer characteristic of the interior of the receptacle.

In an embodiment, the storage device comprises a plurality of the receptacles, optionally in the form of a dossette box. The storage device thus allows the quality, authenticity and/or presence or absence of multiple pharmaceutical products to be monitored simultaneously. In an embodiment, the storage device is used to monitor correct administration of medicines to a patient.

According to an aspect, there is provided a method of sensing, comprising: using a sensor element to apply a heating pulse to a target material; and determining chemical or structural information about the target material by measuring a response of the sensor element during the heating pulse, the response being dependent on a heat transfer characteristic of the target material, wherein: the information about the target material is at least partially obtained from a combination of a first measured response to a heating pulse and a second measured response to a heating pulse; and an average temperature of the region being sensed during obtaining of the first measured response is different from an average temperature of the region being sensed during obtaining of the second measured response.

BRIEF DESCRIPTION OF THE DRAWINGS

Embodiments of the invention will now be described, by way of example only, with reference to the accompanying drawings in which corresponding reference symbols indicate corresponding parts, and in which.

DETAILED DESCRIPTION

Figure 1:
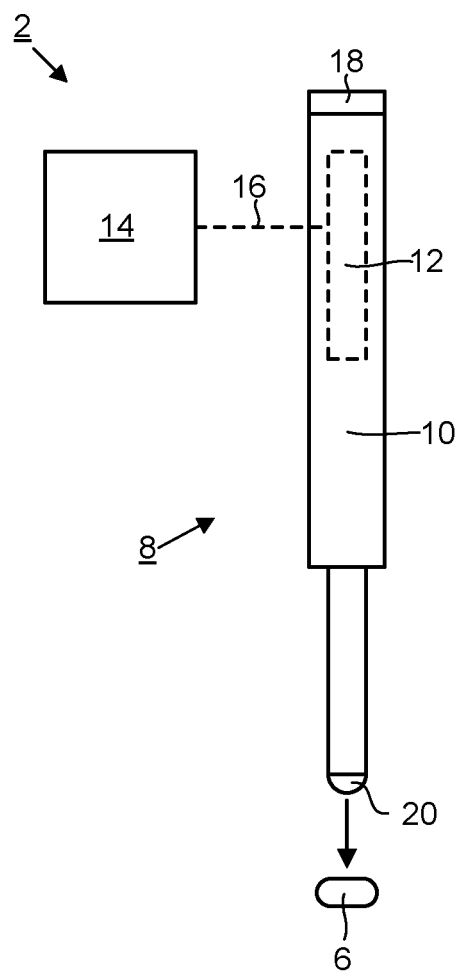
FIG. 1 depicts a probe apparatus according to an embodiment.

Embodiments of the present disclosure provide methods of sensing a pharmaceutical product to obtain compositional information about the pharmaceutical product. The compositional information may comprise any compositional property that affects thermal characteristics, in particular heat transfer characteristics, of the pharmaceutical product. The compositional information may comprising chemical or structural information. The pharmaceutical product may comprise a solid, for example in the form of a tablet or powder. In an embodiment, the pharmaceutical product comprises a solid body for oral administration, the solid body comprising a pharmaceutically active ingredient. In other embodiments, the pharmaceutical product comprises a liquid.

The methods use a sensor element to apply a heating pulse to the pharmaceutical product. A response of the sensor element during the heating pulse is measured. The response is dependent on a heat transfer characteristic of the pharmaceutical product. The heat transfer characteristic depends on chemical and/or structural properties of the pharmaceutical product. The measured response therefore provides information about chemical and/or structural properties of the pharmaceutical product. The heat transfer characteristic affects how efficiently heat will be conducted away from the sensor element. Heat from the heating pulse penetrates underneath the surface of the pharmaceutical product being sensed, allowing sub-surface structure to be sensed, such as different layers of the pharmaceutical product, or inhomogeneities or inclusions within the pharmaceutical product. The methodology is thus sensitive to pharmaceutical products in which an active or other component is distributed within a matrix material having a different composition. The ability to detect sub-structure makes it possible for the sensing to be performed through materials separating the sensor element from the material of interest, including not only outer layers of a pharmaceutical product but also packaging or other materials that may be present around the pharmaceutical product.

Sensing can be achieved effectively even for relatively low energy pulses. The method can be performed for example without increasing the local temperature of the pharmaceutical product by more than about two degrees Celsius. Thermal damage to the pharmaceutical product is therefore avoided.

Heat transfer characteristics of materials (e.g. thermal properties such as thermal conductivity, $\kappa$, specific heat capacity, $c$, and quantities that depend on one or both of these properties) can depend sensitively on the composition (e.g. chemical or structural) of the materials. The thermal product, $\sqrt{\rho c \kappa}$, where $\rho$ is equal to the density, is often a heat transfer characteristic that is particularly sensitive to composition because it takes into account both $\kappa$ and $c$. Changes in either or both of $\kappa$ and $c$ will typically result in a change in $\sqrt{\rho c \kappa}$. Changes in relative concentrations of different components in a multi-component material can be detected where the different components have different thermal properties. Changes in structure can be detected where there is a density or compositional change.

Figure 2:
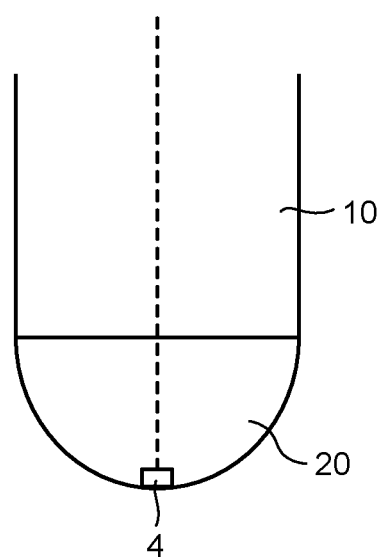
FIG. 2 is a magnified view of a sensor element region of the probe apparatus of FIG. 1.

FIGS. 1 and 2 depict an example probe apparatus 2 for performing the method. The probe apparatus 2 comprises a sensor element 4 (shown in FIG. 2). The sensor element 4 is configured to be brought into thermal contact with a pharmaceutical product 6 to be sensed. In the embodiment shown, the sensor element 4 is provided at the distal end of a probe 8. The probe 8 comprises a handle 10. A user can bring the sensor element 4 into thermal contact with a pharmaceutical product 6 to be sensed while holding the probe 8 by the handle 10. The probe 8 may have a shape and/or size that is similar to a writing pen, for example.

The probe 8 comprises a measurement unit 12. The measurement unit 12 applies a heating pulse to the pharmaceutical product 6 via the sensor element 4. The measurement unit 12 further measures a response of the sensor element 4 during the heating pulse. The response is dependent on a heat transfer characteristic of the pharmaceutical product 6, as discussed above. Example circuitry for implementing the measurement unit 12 is discussed below with reference to FIG. 13.

The probe apparatus 2 further comprises a data processing unit 14. The measurement unit 12 communicates with the data processing unit 14 via data connection 16 (wired or wireless). In the embodiment shown, the data processing unit 14 is a device that is separate from the probe 4, but the data processing unit 14 could also be incorporated into the probe 8. The data processing unit 14 may be configured to perform the required data processing tasks using any suitable hardware, firmware and/or software, including any known computational hardware (e.g. CPU, RAM, storage devices, etc.). Either or both of the measurement unit 12 and data processing unit 14 may comprise a power supply and data processing hardware to control the supply of the heating power and to control the measurement process. Either or both of the measurement unit 12 and data processing unit 14 may be connected to mains power or be powered by a battery. Either or both of the measurement unit 12 and data processing unit 14 may comprise a memory for storing measurements and/or calibration data for analysing measurements.

Data and/or signals representing the measured response of the sensor element 4 may be transferred to the data processing unit 14. The data processing unit 14 compares the measured response or chemical or structural information determined from the measured response with a stored reference response obtained at a previous time from a reference pharmaceutical product or with stored chemical or structural information about the reference pharmaceutical product. The data processing unit 14 may be implemented by a personal computer, tablet, or smartphone.

In one implementation, the probe is provided with a user input unit 18 (e.g. a button). A user positions the probe 8 so that the sensor element 4 is in thermal contact with a reference pharmaceutical product (e.g. a product known to be of acceptable quality and/or authentic). The user provides an input to the probe 8 via the user input unit 18 (e.g. by pressing a button) to cause the probe 8 to measure the reference pharmaceutical product by applying a heating pulse to the sensor element 4. The response of the sensor element 4 is stored (either in the probe 4 or in the data processing unit 14). The user then repositions the probe 8 so that the sensor element 4 is in thermal contact with a pharmaceutical product to be tested. The user provides a further input to the probe 8 via the user input unit 18 (e.g. by pressing a button) to cause the probe 8 to measure the pharmaceutical product to be tested. The data processing unit 14 compares the measured response from the pharmaceutical product to be tested with the measured response from the reference pharmaceutical product. The probe apparatus 2 provides an output to the user that provides information about the result of the comparison. For example, if the chemical and/or structural composition of the pharmaceutical product to be tested is close enough to that of the reference pharmaceutical product, the output may indicate that the pharmaceutical product to be tested has passed the test (and is therefore of sufficiently high quality, where the testing is being done as part of a quality control procedure, or is authentic, wherein the testing is being done to detect fake versions of the pharmaceutical product). In contrast, where the chemical and/or structural composition of the pharmaceutical product to be tested is different by more than a threshold amount from that of the reference pharmaceutical product, the output may indicate that the pharmaceutical product to be tested has not passed the test (and is therefore of sub-standard quality or is a suspected fake). The probe 8 and/or data processing unit 14 may be provided with a display to provide a visual indication of the result of the comparison to the user. A traffic light system may be used, for example, where green represents passing of the test, red represents failure of the test, and amber (which may be optional) indicates a marginal result. The above process may be automated to speed up the checking procedure, for example in the context of quality control in a manufacturing facility. In this context, and others, the probe apparatus 2 would not need a handle 10 to allow manual manipulation by a user.

In an embodiment, the probe apparatus 2 comprises a deformable coupling member 20 that deforms on engagement with the pharmaceutical product 6 when the probe 8 is brought into contact with the pharmaceutical product 6. The sensor element 4 is mounted on, in, and/or in thermal contact with, the deformable coupling member 20. The deformable coupling member 20 may be configured to deform elastically (e.g. such that the deformable coupling member 20 is resilient and springs back to an equilibrium shape when the contact between the probe 8 and the pharmaceutical product 6 is removed). In an embodiment, the deformable coupling member 20 comprises a foam material or a deformable membrane (pocket) comprising a fluid such as air. An example arrangement is shown in FIG. 2, where the sensor element 4 is provided on or near a distal surface of the deformable coupling member 20. The broken line indicates schematically an electrical connection path from the sensor element 4 towards the measurement unit 12. The electrical connection path may pass through or around the deformable coupling member 20 depending on the nature of the deformable coupling member 20. Where the deformable coupling member 20 comprises a membrane containing a fluid such as air, the electrical connection path may comprise metallic tracks formed on a surface of the membrane.

The deformable coupling member 20 helps a user to maintain a suitable force between the probe 8 and the pharmaceutical product 6 during testing, thereby improving accuracy and repeatability of the measurements.

Figure 3:
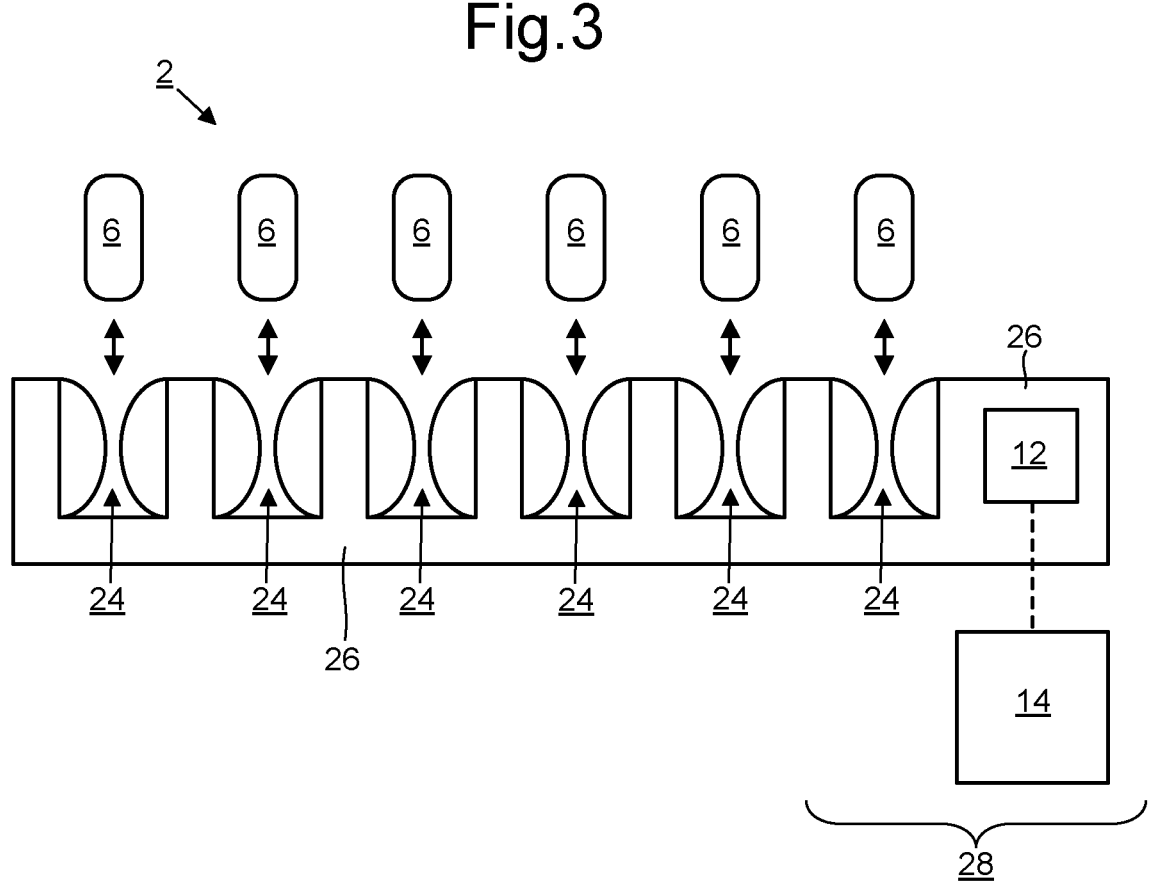
FIG. 3 depicts a probe apparatus comprising a plurality of receptacles.
Figure 4:
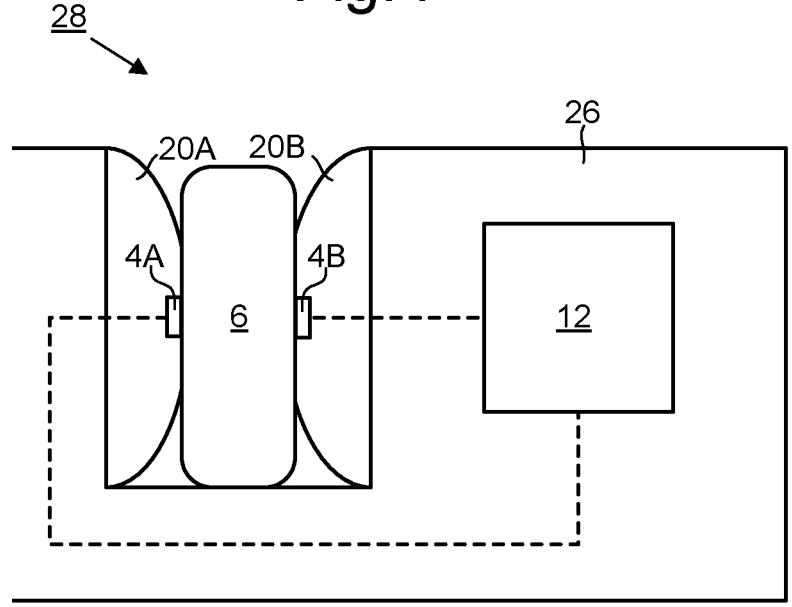
FIG. 4 is a magnified view of an end of the probe apparatus of FIG. 3 comprising a first of the receptacles and a measurement unit.

FIGS. 3 and 4 depict an alternative probe apparatus 2. The probe apparatus 2 comprises a sensor element 4, measurement unit 12 and data processing unit 14 configured to operate substantially as described above with reference to FIGS. 1 and 2. The probe apparatus 2 additionally comprises a receptacle 24 configured to receive a pharmaceutical product 6. In the particular example shown, the probe apparatus 2 comprises a plurality of such receptacles 24, each receptacle configured to receive a pharmaceutical product 6. Within each receptacle 24, a sensor element 4A,4B is configured to engage against a pharmaceutical product 6 located within the receptacle 24. In the particular example shown, each receptacle 24 comprises two sensor elements 4A and 4B (see FIG. 4), but each receptacle could also be provided with only a single sensor element or more than two sensor elements. The receptacles 24 may be formed as wells in a substrate 26.

FIG. 4 shows an end region 28 of the probe apparatus of FIG. 3, including a first of the receptacles 24 and the measurement unit 12. A pharmaceutical product 6 is present in the receptacle 24. The probe apparatus 2 comprises a deformable coupling member 20A,20B configured to deform on engagement with the pharmaceutical product 6 when the pharmaceutical product 6 is in the receptacle 24 (as shown in FIG. 4). The sensor element 4A,4B is mounted on, in, and/or in thermal contact with, the deformable coupling member 20A,20B. In the particular arrangement shown in FIGS. 3 and 4, two deformable coupling members 20A and 20B are provided per receptacle 24. Each of the deformable coupling members 20A,20B may be configured as described above with reference to FIGS. 1 and 2, and serves the same purpose of providing reliable thermal contact between a sensor element 4A,4B and the pharmaceutical product 6 to be tested. Broken lines depict electrical connection paths between the sensor elements 4A,4B and the measurement unit 12. In the embodiment shown, the deformable coupling members 20A,20B are mounted within each receptacle 24 in such a way that a pharmaceutical product 6 present in the receptacle 24 is squeezed between the two deformable coupling members 20A,20B. A force applied to the pharmaceutical product 6 from each side thus depends purely on the geometries of the pharmaceutical product 6 and the two deformable coupling members 20A,20B (and not on any user applied force). Where these geometries are the same for different pharmaceutical products and different receptacles, the corresponding forces and quality of thermal contacts will be identical. Accurate and reproducible measurement and/or comparison of products in different receptacles 24 is thereby facilitated.

Figure 5:
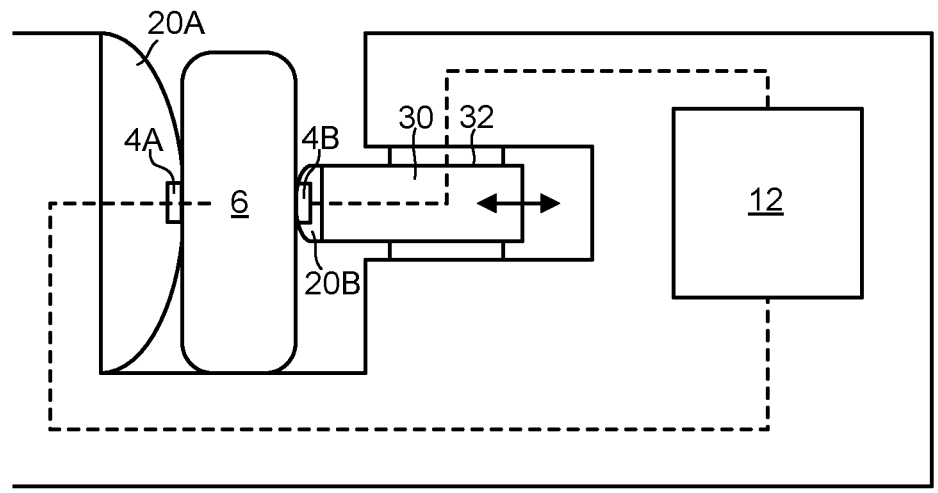
FIG. 5 is a magnified view of an alternative receptacle in which a sensor element is movable mounted.

In a variation on the embodiment of FIGS. 3 and 4, one or more of the receptacles 24 is configured so that a sensor element 4B is movably mounted. The probe apparatus 2 may then drive the sensor element 4B actively against the pharmaceutical product 6 in the receptacle 24 (i.e. not simply via resilience of a deformable coupling member). Alternatively or additionally, the probe apparatus 2 may be configured such that a user can drive the sensor element 4B against the pharmaceutical product 6 in the receptacle 24 (e.g. by pressing against a piston on which the sensor element 4B is mounted). Alternatively or additionally, the probe apparatus 2 may be configured such that gravity can drive the sensor element 4B against the pharmaceutical product 6 in the receptacle 24 (e.g. by mounting the sensor element 4B on a piston and using the weight of the piston to drive the sensor element 4B against the pharmaceutical product 6). An example arrangement is shown in FIG. 5, which shows the region 28 as depicted in FIG. 4 except that in this embodiment the sensor element 4B is movably mounted and configured to be driven actively against the pharmaceutical product 6. In this embodiment, the sensor element 4B is mounted at the distal end of a piston 30 configured to move longitudinally within guide cylinder 32. A driving unit applies a force (e.g. electromagnetically) to the piston 30 to drive movement of the piston 30 until the sensor element 4B is pressed against the pharmaceutical product 6 with the desired force. The sensor element 4B is mounted on a deformable coupling member 20B as in previous embodiments. The provision of an actively movable sensor element 4B allows the probe apparatus 2 to accommodate a wider range of sizes of pharmaceutical product 6 within the receptacle 24 and/or provides a higher degree of control of the force of contact between the sensor element 4B or deformable coupling member 20B and the pharmaceutical product 6.

In an embodiment, information about the pharmaceutical product 6 is obtained from a combination of a first measured response to a heating pulse and a second measured response to a heating pulse. The first and second measured responses are obtained in such a way that an average temperature within a corresponding sensed region of the pharmaceutical product 6 (and/or, therefore, of the sensor element) during obtaining of the first measured response is different from an average temperature within a corresponding sensed region of the pharmaceutical product 6 (and/or, therefore, of the sensor element) during obtaining of the second measured response. In an embodiment, the information obtained in this way from the combination of the first measured response and the second measured response comprises information about the density of the pharmaceutical product 6. This information can be obtained for differences in temperature that are relatively small, optionally less than 10 degrees C., optionally less than 5 degrees C., optionally less than 2 degrees C. Detailed information about the pharmaceutical product 6 can thus be obtained with no or minimal risk of damaging the pharmaceutical product 6. Even vaccines, which generally need to be kept within a specified temperature range (e.g. between 2-8 degrees C.), can be tested safely.

In an embodiment, the first measured response is obtained during application by the sensor element 4 or a plurality of the sensor elements 4A,4B of a first heating pulse to the pharmaceutical product 6. The second measured response is obtained during application by the sensor element 4 or by a plurality of the sensor elements 4A,4B of a second heating pulse to the pharmaceutical product 6. The first and second heating pulses can thus be applied by the same sensor element 4 or by different sensor elements 4A,4B. In the case where the first and second heating pulses are applied using different sensor elements 4A,4B, it is possible for them to be applied at the same time or during overlapping time periods. In an embodiment the first and second heating pulses have the same duration but either start from a higher sensed region temperature or have different input powers, such that the sensed region is heated at different rates during the first and second heating pulses. The magnitude of a change in temperature of the sensed region during the first heating pulse may thus be different to the magnitude of a change in temperature of the sensed region during the first heating pulse, for example by a factor of 2 or more.

FIGS. 3-5 depict example embodiments in which two sensor elements 4A and 4B are provided that are capable of applying the first and second heating pulses simultaneously or in overlapping time periods. The embodiments of FIGS. 3-5 could also be provided with only a single sensor element per receptacle where it is not desired to provide first and second heating pulses simultaneously or in overlapping time periods. In the embodiments shown, each of one or more receptacles 24 are provided with a first sensor element 4A and a second sensor element 4B. The first sensor element 4A is used to apply the first heating pulse to the pharmaceutical product 6. The first heating pulse is such that a sensed region of the pharmaceutical product 6 has a first average temperature during the first heating pulse. The second sensor element 4B is used to apply the second heating pulse to the pharmaceutical product 6. The second heating pulse is such that the sensed region of the pharmaceutical product 6 has a second average temperature during the second heating pulse. The first and second heating pulses are applied to the pharmaceutical product 6 at different positions (either simultaneously or at different times or during completely or partially overlapping time periods).

The combination of the first measured response and the second measurement response may be used to derive information about the density of the pharmaceutical product because of the typically much smaller temperature variation of density $\rho$ in comparison to other factors affecting heat transfer characteristics of the pharmaceutical product, such as heat capacity c and thermal conductivity $\kappa$. The response of the sensor element 4A,4B depends on the thermal product $\sqrt{\rho c \kappa}$ of the pharmaceutical product 6. The first and second measured responses provide information about the thermal product at two different temperatures. For the relatively small differences in temperature involved it is expected that $\rho$ will not change significantly while either or both of c and $\kappa$ will change significantly. The two measurements provide two independent equations from which c $\kappa$ can be eliminated to determine information about the density $\rho$. Thus, fake or sub-standard pharmaceutical products that have the correct thermal product but an incorrect density can be detected. When detecting the difference between two different products or between a product under test and reference data, it is not even necessary explicitly to determine density. Any significant difference in density between the test product and the reference product or data would result in a difference between the measured thermal products for at least one of the measurements at different temperatures.

Figure 14:
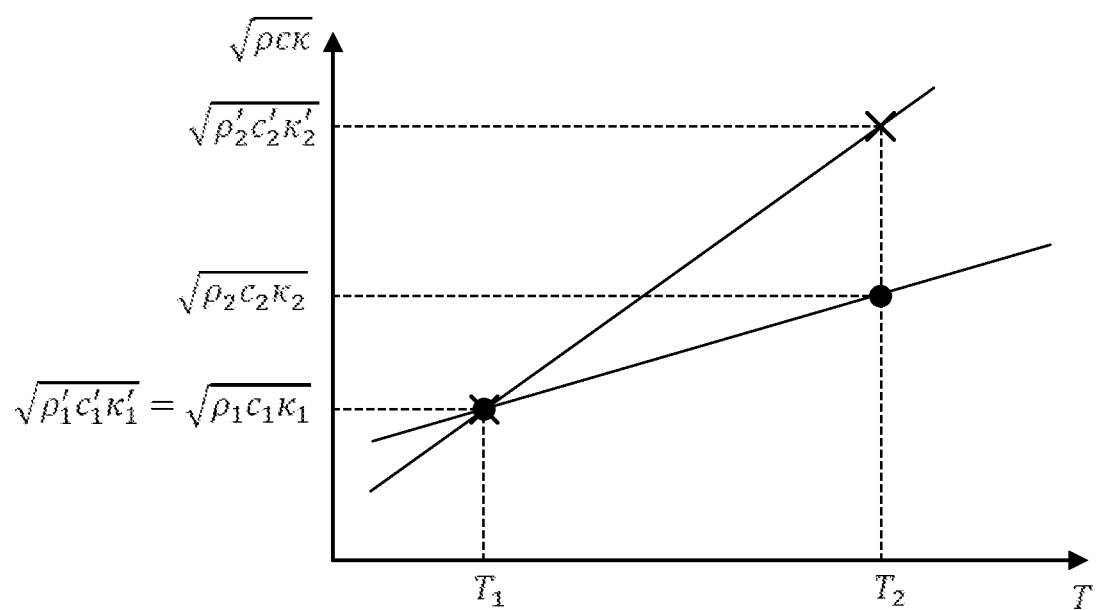
FIG. 14 is a graph depicting thermal product measurements obtained at different temperatures for a notional genuine pharmaceutical product and a notional counterfeit pharmaceutical product.

FIG. 14 is a graph depicting artificially generated data representing typical expected results obtained from performing measurements on a counterfeit product and on a reference product at two different temperatures $T_1$ and $T_2$. The vertical axis represents a determined heat transfer characteristic of the product, in this case thermal product $\sqrt{\rho c \kappa}$. At $T_1$, the thermal product of the counterfeit product, $\sqrt{\rho'_1 c'_1 \kappa'_1}$, is exactly the same as the thermal product of the reference product, $\sqrt{\rho_1 c_1 \kappa_1}$. The two products therefore appear identical. Indeed, the counterfeit manufacturer may have deliberately manipulated the density of the counterfeit product to achieve this result, for example by compacting the product. However, by measuring the thermal product at different temperatures, it is possible to distinguish between the two products and thereby detect that the counterfeit product is not genuine. Since density is a very weak function of temperature, relative to c and $\kappa$, then only if the value of $c*\kappa$ is correctly matched to the genuine product will the counterfeit give the correct graph of thermal product vs temperature, which is determined by the dependency of $c(T)*\kappa(T)$. In the particular example shown in FIG. 14, therefore, while $\sqrt{\rho'_1 c'_1 \kappa'_1} = \sqrt{\rho_1 c_1 \kappa_1}$, $\rho_1 \approx \rho_2$, and $\rho'_1 \approx \rho'_1$, $c_1 \kappa_1 \neq c_2 \kappa_2$. Therefore, the thermal products at $T_2$ differ: $\sqrt{\rho'_2 c'_2 \kappa'_2} \neq \sqrt{\rho_2 c_2 \kappa_2}$.

The approach of taking the measurements at different temperatures of the sensed region can be extended beyond applications to pharmaceutical products to target materials of other types, thereby providing corresponding advantages in other fields. The measurements may for example by applied to quality control procedures or to detecting counterfeit products in other fields.

Figure 6:
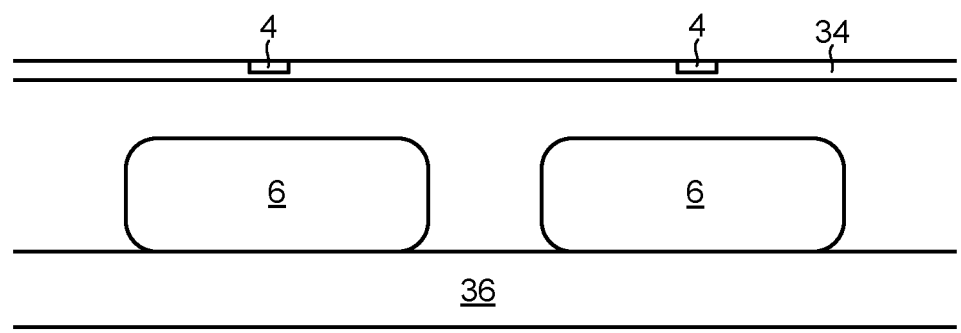
FIG. 6 depicts tablets located between a substrate and a film containing sensor elements.
Figure 7:
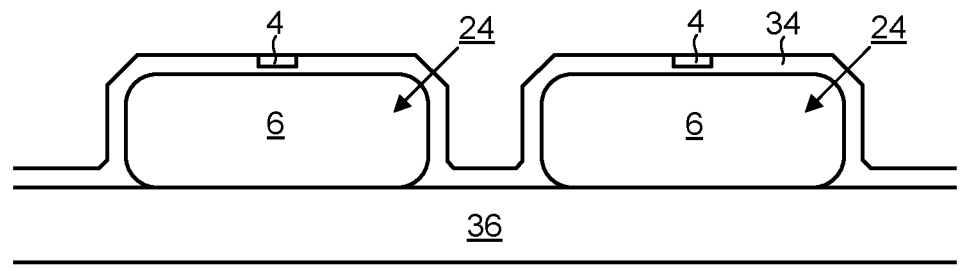
FIG. 7 depicts the arrangement of FIG. 6 after the film has been brought into contact with the tablets by applying a vacuum to the region between the film and the substrate.

FIGS. 6 and 7 depict an alternative embodiment in which receptacles 24 are formed by vacuum packing pharmaceutical products 6 under a film 34. FIG. 6 depicts example pharmaceutical products 6 supported by a substrate 36 with a film 34 positioned above. The substrate 36 may or may not contain wells to localize the pharmaceutical products 6 prior to application of the vacuum. FIG. 7 depicts the arrangement of FIG. 6 after vacuum has been applied to the region between the substrate 36 and the film 34, thereby causing the pharmaceutical products 6 to be encapsulated by the film 34 on one side and the substrate 36 on the other. A sensor element 4 is provided on or in the film 34. The sensor element 4 is brought into engagement against the pharmaceutical product 6 by the pressing of the film 34 against the pharmaceutical product 6 caused by the application of the vacuum, as depicted in FIG. 7. Alternatively, a sensor element may be brought into contact with the film 34 from outside of the film, and sensing of the pharmaceutical product may be performed entirely from outside of the packaged product.

In an embodiment, a storage device for a pharmaceutical product 6 is provided. The storage device may comprise any of the elements discussed above with reference to FIGS. 3-7 except that a data processing unit 14 is not required as part of the storage device itself. The storage device may thus store pharmaceutical products 6 and allow the stored pharmaceutical products 6 to be tested or monitored when required. The storage device comprises at least one receptacle 24, typically a plurality of the receptacles 24. The storage device may take the form of a dossette box, for example. The storage device comprises a measurement unit 12 as described above. The measurement unit 12 allows the contents of the storage device to be tested or monitored. The measurement unit 12 allows the quality, authenticity and/or presence or absence of multiple pharmaceutical products to be monitored simultaneously. In an embodiment, the storage device is used to monitor correct administration of medicines to a patient. These functionalities may be provided by a data processing unit 14 that communicates with the measurement unit 12, for example wirelessly from a transmitter provided in the storage device itself or via a docking station configured to receive the storage device. Alternatively the data processing unit 14 may be incorporated into the storage device. In an embodiment, the data processing unit 14 compares the measured response with stored reference data to determine information about a pharmaceutical product present in a receptacle 24 or to detect whether a predetermined pharmaceutical product 6 is present in a receptacle 24.

In an embodiment, the sensor element 4,4A,4B comprises a resistive element. The heating pulse is applied by driving an electrical current through the resistive element to create Joule heating. The response of the sensor element 4,4A,4B during the heating pulse is determined by the measurement unit 12 by measuring an electrical response of the resistive element to the heating pulse. The measured electrical response may be proportional to a resistance of the resistive element or to a quantity that is dependent on the resistance of the resistive element.

In an embodiment, the measurement unit 12 applies a plurality of the heating pulses. Each heating pulse is applied by driving an electrical current through the resistive element. In an embodiment, top hat shaped pulses are applied, but other pulse shapes could be used if desired. In an embodiment, the plurality of heating pulses each have the same duration. The heating pulses are regularly spaced apart from each other (i.e. the spacing between each pair of heating pulses is the same). The duration of each heating pulse is equal to or less than the separation between the heating pulses. This provides time for the resistive element to cool between each heating pulse. In an embodiment, the separation between heating pulses is the same as the duration of each heating pulse. This provides a minimum time for the resistive element to cool between heating pulses, thereby allowing a high measurement sampling rate and, as a consequence, high accuracy (by averaging) and/or time resolution.

The measurement unit 12 measures an electrical response of the resistive element to the heating pulses, for example by measuring a voltage dependent on the resistance of the resistive element and the current being driven through the resistive element. The resistance of the resistive element varies as a function of the temperature of the resistive element. Measuring the electrical response of the resistive element thus corresponds to measuring a temperature response of the resistive element.

The electrical response of the resistive element to the heating pulses can be used to determine chemical and/or structural information about materials adjacent to the resistive element because the variation in the temperature of the resistive element with time will depend on the heat transfer characteristics of those materials.

In an embodiment, a response to the heating pulse is compared with the response to a corresponding heating pulse applied to a reference material. The size of the response, the variation of the response as a function of time, or various other aspects of the response may be considered. Any deviation from the response measured for the reference material may be used to detect a deviation from normality for the pharmaceutical product being sensed. The nature of the heating pulses may be selected to achieve optimum sensitivity for the particular type of pharmaceutical product being measured. This may involve selecting particular pulse shapes, amplitudes, durations and/or repetition rates, for example.

In an embodiment, the resistive element is mounted on a substrate in such a way that at least 10% of the surface area of the resistive element is in contact with the substrate, optionally via a support material encapsulating the resistive element (e.g. a thin film of electrically insulating material), optionally more than 30%, optionally around 50%. In an embodiment, the substrate may form part of a deformable coupling member 20,20A,20B. In an embodiment the resistive element is a thin film resistive element (e.g. thin film resistance thermometer). In an embodiment the resistive element comprises a thin film of platinum or gold mounted on the substrate (e.g. deformable coupling member 20,20A, 20B). In an embodiment, the resistive element has a first surface configured to face towards the pharmaceutical product to be sensed and a second surface facing towards the substrate. It is understood that the first and second surfaces are the large surfaces of the thin film (and do not include any of the very thin side surfaces). In an embodiment no portion of the entity being sensed is present between the second surface and the substrate. Substantially 50% of the surface of the resistive element is in contact with the substrate 14. The presence of the substrate 14 allows relatively large currents to be applied to the resistive element without the resistive element overheating, which could damage the resistive element and/or material that is in contact with the resistive element.

In various embodiments the resistive element is metallic. In these embodiments, the resistive element may be configured such that the thermal contact between the resistive element and the pharmaceutical product being sensed will not result in a significant reduction in the electrical resistance between one end of the resistive element and the other end of the resistive element. This may be achieved by arranging for the resistivity of the resistive element to be much lower than the resistivity of the entity to be sensed or by positioning a thin layer of electrically insulating material between the resistive element and the entity to be sensed.

In an embodiment, heat from the heating pulse propagates through plural layers of different structural or chemical composition and the analysis of the response makes it possible to distinguish between contributions from different layers. In embodiments of this type, the response from the sensor element 4 may be analysed to identify one or more target time periods. Each target time period is a time period in which the response to the heating pulse is determined predominantly by a different combination of one or more of the plural layers. The determined chemical or structural information may thus comprise a variation as a function of distance from the sensor element 4 of the chemical or structural composition of the pharmaceutical product.

In an embodiment, a coupling fluid or gel is provided between the sensor element and the pharmaceutical product under test during application of the heating pulse to the pharmaceutical product. The coupling fluid or gel helps reproducibly to provide a high quality thermal contact between the sensor element and the pharmaceutical product. The coupling fluid or gel will in general have heat transfer characteristics different from those of the pharmaceutical product being sensed. These different properties make it possible to recognize which part of the response of the sensor element is due solely to the coupling fluid or gel and which part provides information about the pharmaceutical product.

FIGS. 8-12 depict example responses from a sensor element 4 comprising a thin film resistive element. The responses consist of a variation of a voltage across the resistive element during a time interval in which a heating pulse of duration $5 \times 10^{-3}$ s is being applied to various different pharmaceutical products.

Figure 8:
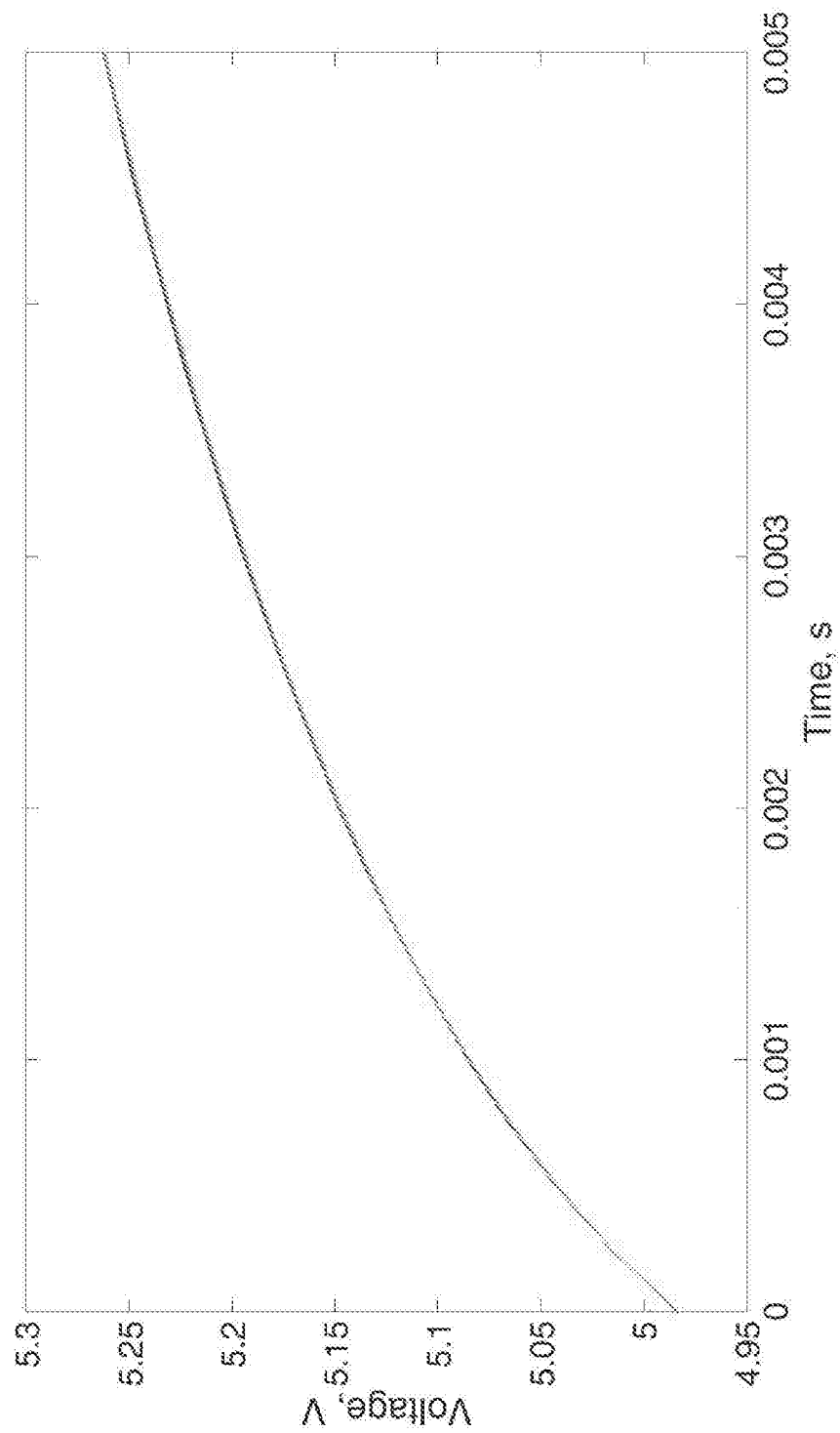
FIG. 8 is a graph showing a measured sensor element response during a heating pulse applied in six separate measurements of paracetamol tablets from the same supplier and same batch.

FIG. 8 is a graph showing a measured sensor element response during a heating pulse applied in six separate measurements of paracetamol tablets from the same supplier and same batch. The six responses lie almost perfectly on top of each other, indicated a high level of consistency both in the composition of the tablets and in the measurement method.

Figure 9:
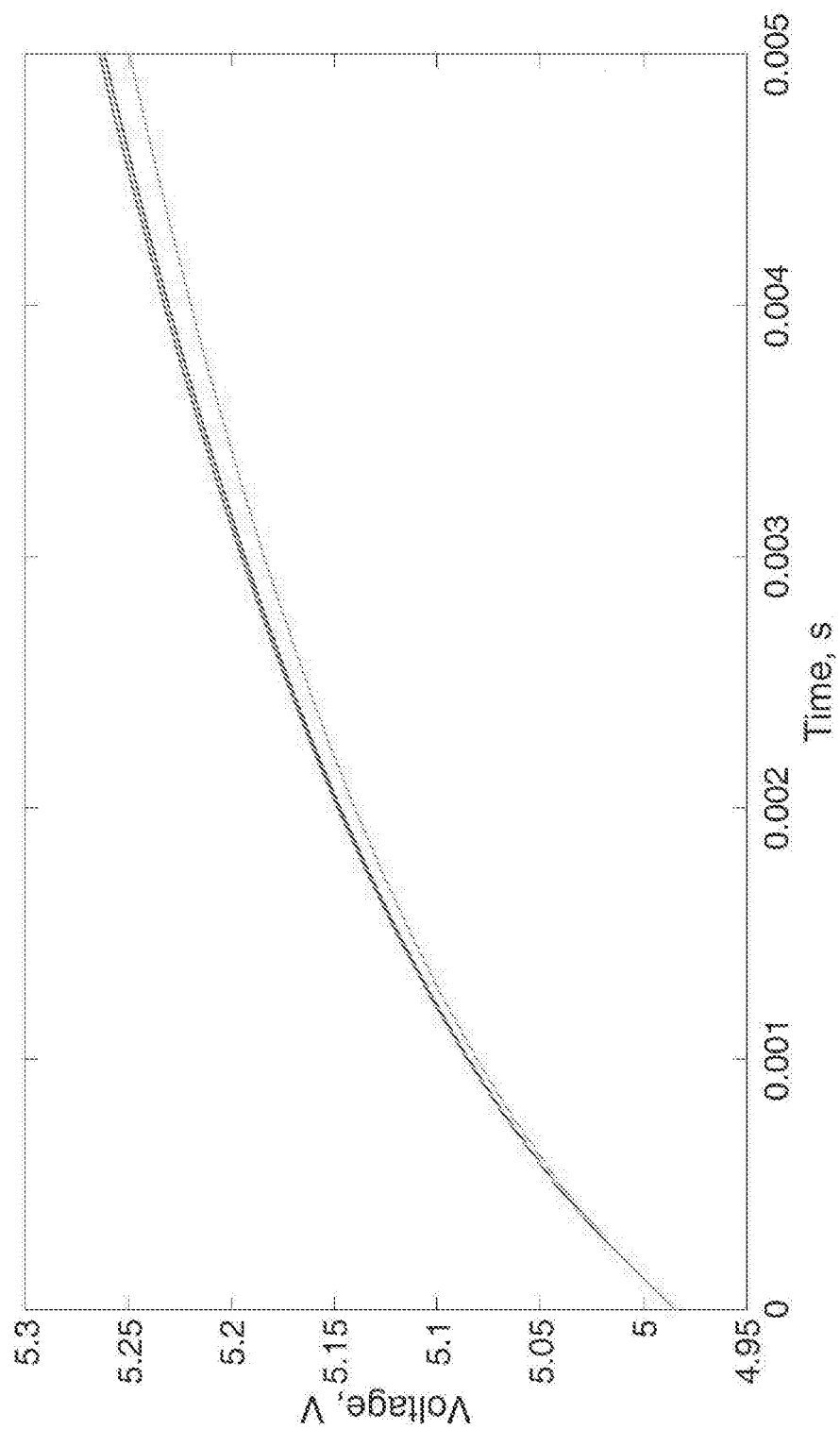
FIG. 9 is a graph showing a measured sensor element response during a heating pulse applied in three separate measurements, including two measurements of paracetamol tablets from the same supplier but different batches, and one measurement of paracetamol tablets from a different supplier.

FIG. 9 is a graph showing a measured sensor element response during a heating pulse applied in three separate measurements, including two measurements of paracetamol tablets from the same supplier but different batches (the two uppermost curves), and one measurement of paracetamol tablets from a different supplier (the lowermost curve). In contrast to the situation in FIG. 8, clear differences are seen between all three different types of tablet. The method is thus sensitive enough not only to detect differences between tablets of the same overall type (i.e. paracetamol in this example) from different suppliers (i.e. the difference between the two lowermost curves) but also to detect differences between batches of tablets of the same type from the same supplier (i.e. differences between the two uppermost curves).

Figure 10:
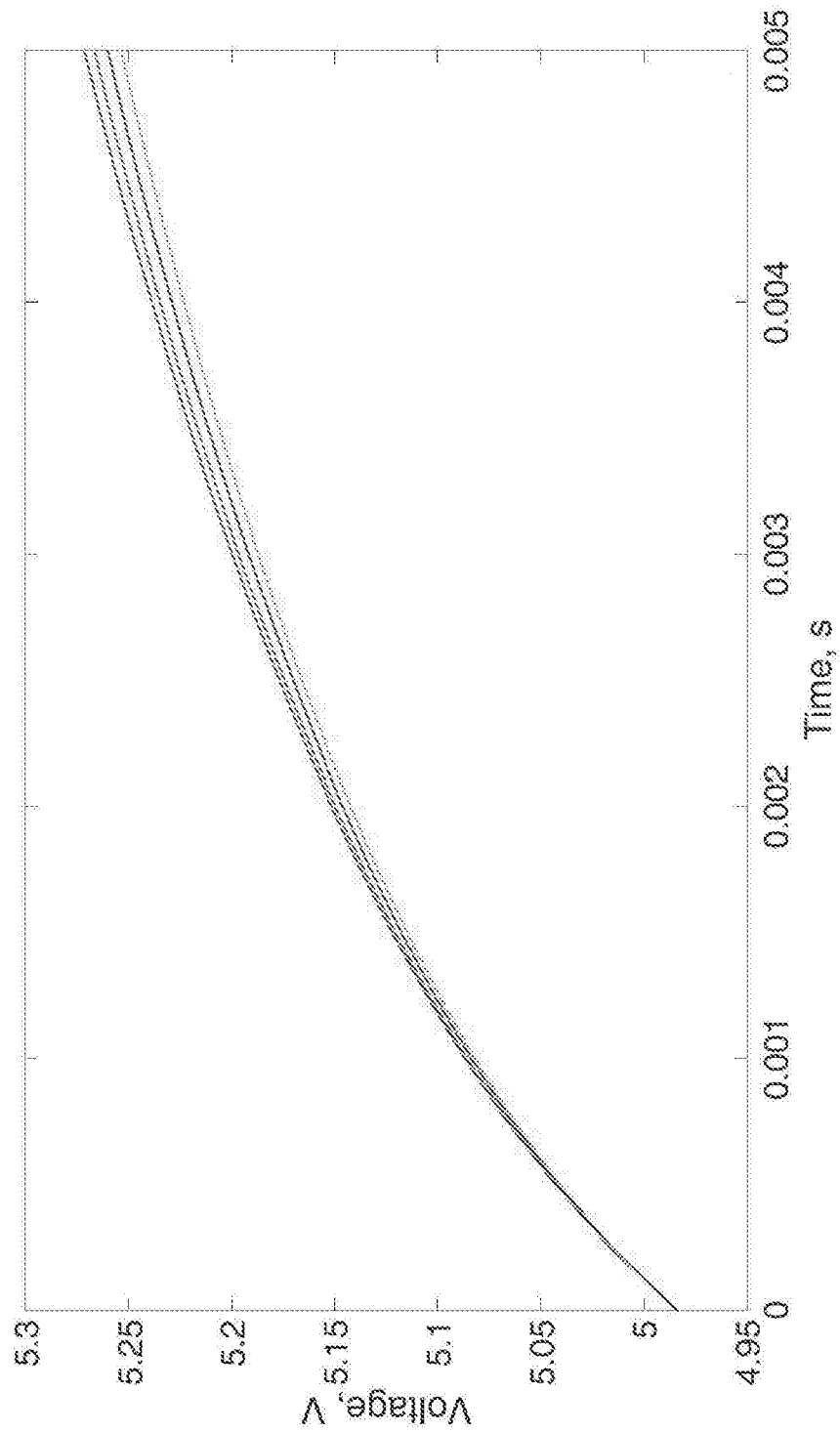
FIG. 10 is a graph showing a measured sensor element response during a heating pulse applied in four separate measurements, including two measurements of ibuprofen tablets from the same supplier but different batches, and two measurement of ibuprofen from different suppliers.

FIG. 10 is a graph showing a measured sensor element response during a heating pulse applied in four separate measurements, including two measurements of ibuprofen tablets from the same supplier but different batches (the two uppermost curves), and two measurement of ibuprofen from different suppliers (the two lowermost curves). Clear differences are seen between all of the different types of tablet, further demonstrating the ability of the method to detect small differences between tablets.

Figure 11:
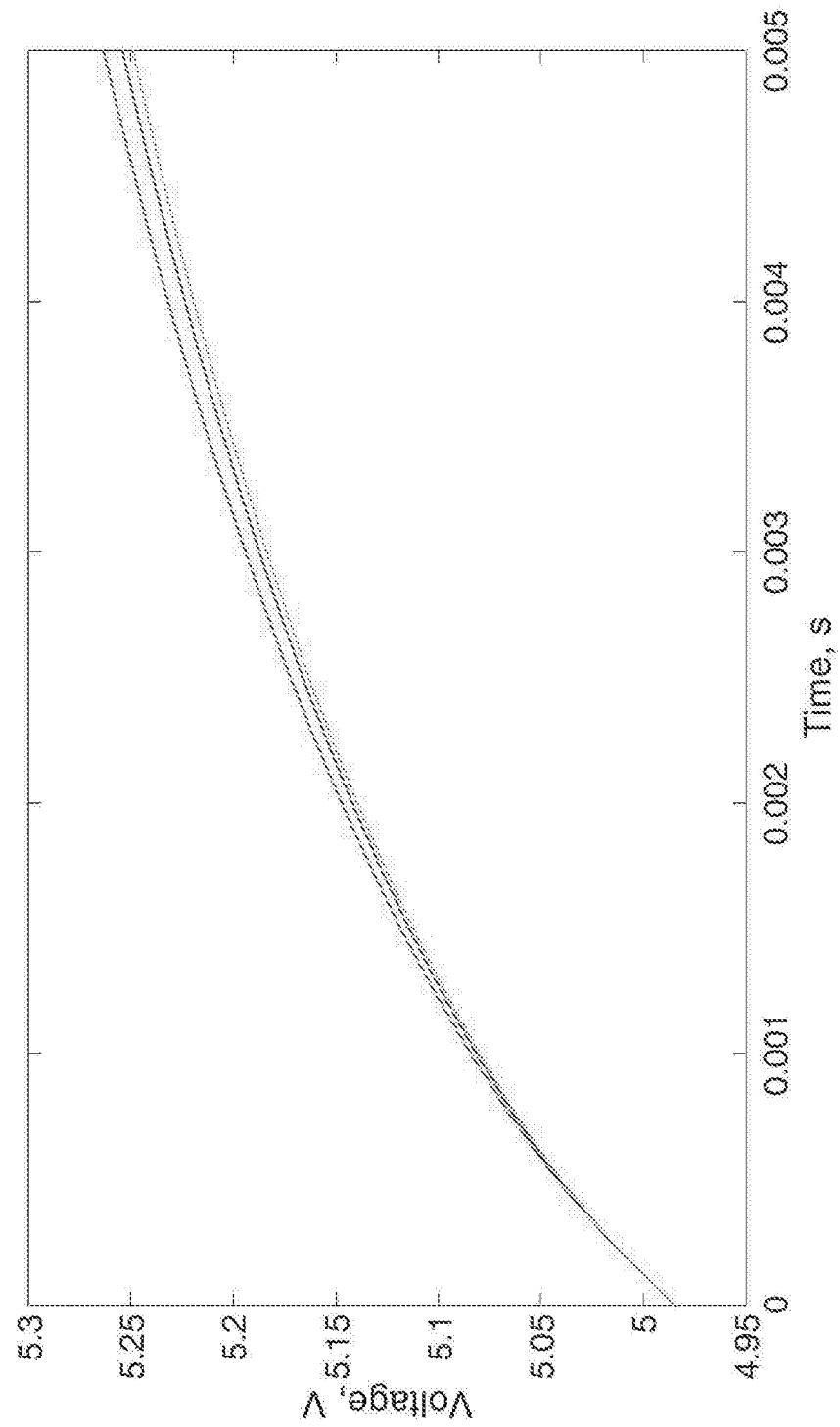
FIG. 11 is a graph showing a measured sensor element response during a heating pulse applied in three separate measurements, including two measurements of antihistamine tablets with the same active ingredient from the same supplier but different batches, and one measurement of antihistamine tablets with the same active ingredient from a different supplier.

FIG. 11 is a graph showing a measured sensor element response during a heating pulse applied in three separate measurements, including two measurements of antihistamine tablets with the same active ingredient from the same supplier but different batches (the two uppermost curves), and one measurement of antihistamine tablets with the same active ingredient from a different supplier (the lowermost curve). Clear differences are seen between all of the different types of tablet, further demonstrating the ability of the method to detect small differences between tablets.

Figure 12:
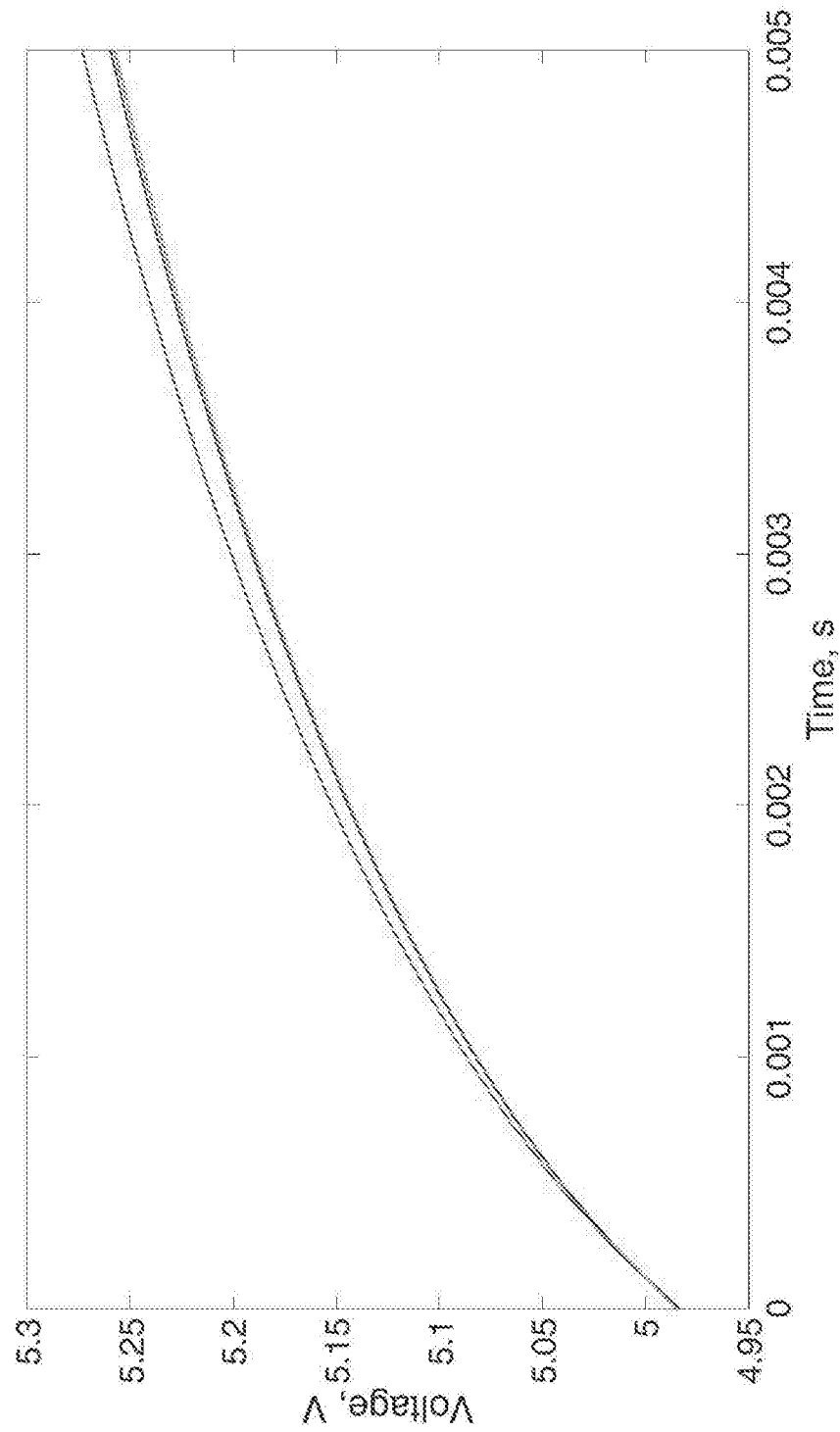
FIG. 12 is a graph showing a measured sensor element response during a heating pulse applied in four separate measurements, each measurement being a measurement of an antihistamine tablet from a different batch, but with the same active ingredient and from the same supplier.

FIG. 12 is a graph showing a measured sensor element response during a heating applied in four separate measurements, each measurement being a measurement of an antihistamine tablet from a different batch, but with the same active ingredient and from the same supplier. Here, a clear difference is seen between one of the batches and the other three batches, further demonstrating the ability of the method to detect small differences between tablets. The similarity for three of the batches is thought to indicate that tablets in these batches are, in fact, extremely similar, as intended by the manufacturing process.

The results depicted in FIGS. 8-12 show that subtle differences can be detected between genuine pharmaceutical products of the same nominal type, even where the products are from different batches from the same supplier. These result thus show that the methods disclosed herein are sensitive enough to be used for quality control purposes in a manufacturing facility. The results also demonstrate that the methods are sensitive enough to detect differences between a fake version of a pharmaceutical product and a real version of the pharmaceutical product, where differences in heat transfer characteristics are expected normally to be much greater than differences between batches from a single supplier of a genuine version of the pharmaceutical. The differences in heat transfer characteristic will be particularly large where the fake version has been manufactured using low cost formulations, which will typically have lower amounts of metallic components (which are more expensive) than the genuine product. Metallic components have a particular large influence on thermal product, so their absence or lower concentration will result in a large shift in the measurement response of the sensor element.

Figure 13:
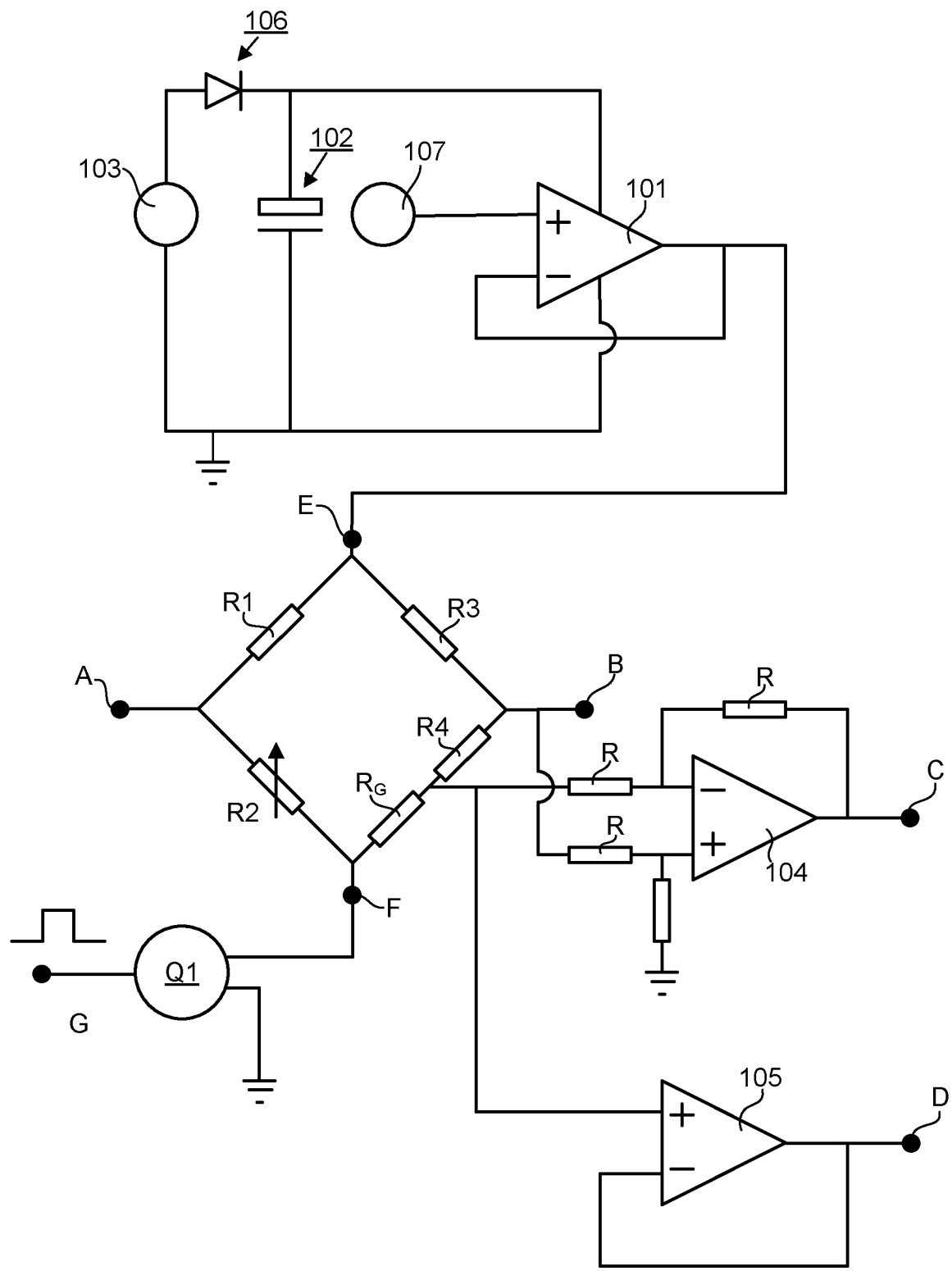
FIG. 13 depicts example circuitry for measuring a response of a sensor element to heating pulses.

FIG. 13 depicts example circuitry for use in the measurement unit 12 for measuring the response of the sensor element 4 to the heating pulses in the case where the sensor element 4 comprises a resistive element. The following elements are shown in FIG. 13:

101 Power amplifier (e.g. about 10 A RATED)
102 Charge store (e.g. about 40,000 μF)
103 Power supply (e.g. about 30V DC)
104 Differential amplifier for I
105 Buffer amplifier for V
R1+R2 Bridge balance
R3+$R_G$ Active bridge half
Q1 Power switch (e.g. fast, low resistance MOSFET)

C Output of current I
D Output of voltage V
E High side of bridge
F Low side of bridge
G Signal pulse control
R4 Current sense shunt (resistance) (e.g. 20 mΩ)
A+B Diagnostic differential signal outputs for development
106 Diode rectifier
107 Voltage reference A voltage generated by voltage supply 103 is fed through a rectifier diode 106 to charge a high capacity storage 102. The storage 102 provides a high current power source to the power amplifier 101. A voltage reference 107 sets a high side voltage presented at E.

A bridge is created between the points A, E, B and F. In an example, R3 and $R_G$ are about 1.0 Ohms, and R1 and R2 are about 470 Ohms. A power switch device Q1 is provided to rapidly bring point F to ground under a signal pulse at G. The circuit enables a steady bridge voltage to be maintained without demanding a high gain bandwidth from the power amplifier 101. The power amplifier 101 needs only to maintain a DC level. High energy pulses of precise timing are made possible using a fast MOSFET power switch for Q1 at the low side of the bridge.

When the bridge is energised the differential voltage points (A & B) will provide a voltage corresponding to the Ohmic resistance change of the gauge element $R_G$ (e.g. the resistive element of the sensor element 4). The other resistors in the bridge are chosen to have a very low parts-per-million (ppm) change in resistance with temperature. Therefore observed bridge voltages are only a function of the gauge $R_G$.

For precise measurements of heat transfer to the resistive element, and from the resistive element to material in contact with the resistive element, it is desirable to measure the voltage V and current I across the resistive element. The current is determined from the output of the circuit at C. The voltage is determined from the output of the circuit at D. Thus the energy input and the corresponding rise in temperature can be determined and the heat transfer function to the material in contact with the resistive element can be computed.

The total energy and energy rate can be controlled by varying the reference voltage 107 and the pulse duration at G.

The circuit allows a modest power source to store energy to deliver very high energy density pulses. Electronic controls may be provided to activate the power level and pulses duration whilst reading the voltage signals at C and D. The electronic controls may be provided by the measurement unit 12 or data processing unit 14, or both.

In an embodiment, fast ADC to storage in computer memory is employed leaving time to compute the heat transfer data from which quantitative measurements can be performed and compared to calibrated lookup tables to provide qualitative assessments of the composition of the pharmaceutical product being sensed.

The above-described embodiments may also be applied to sensing pharmaceutical products that are in liquid form or which comprise liquid. FIGS. 15-18 show example measurements made on a range of different liquid medicines, using a thin film resistive element to generate a measured response. The responses consist of a variation of a voltage proportional to thermal product across the resistive element during a time interval in which a heating pulse of duration $5 \times 10^{-3}$ s is being applied.

Figure 15:
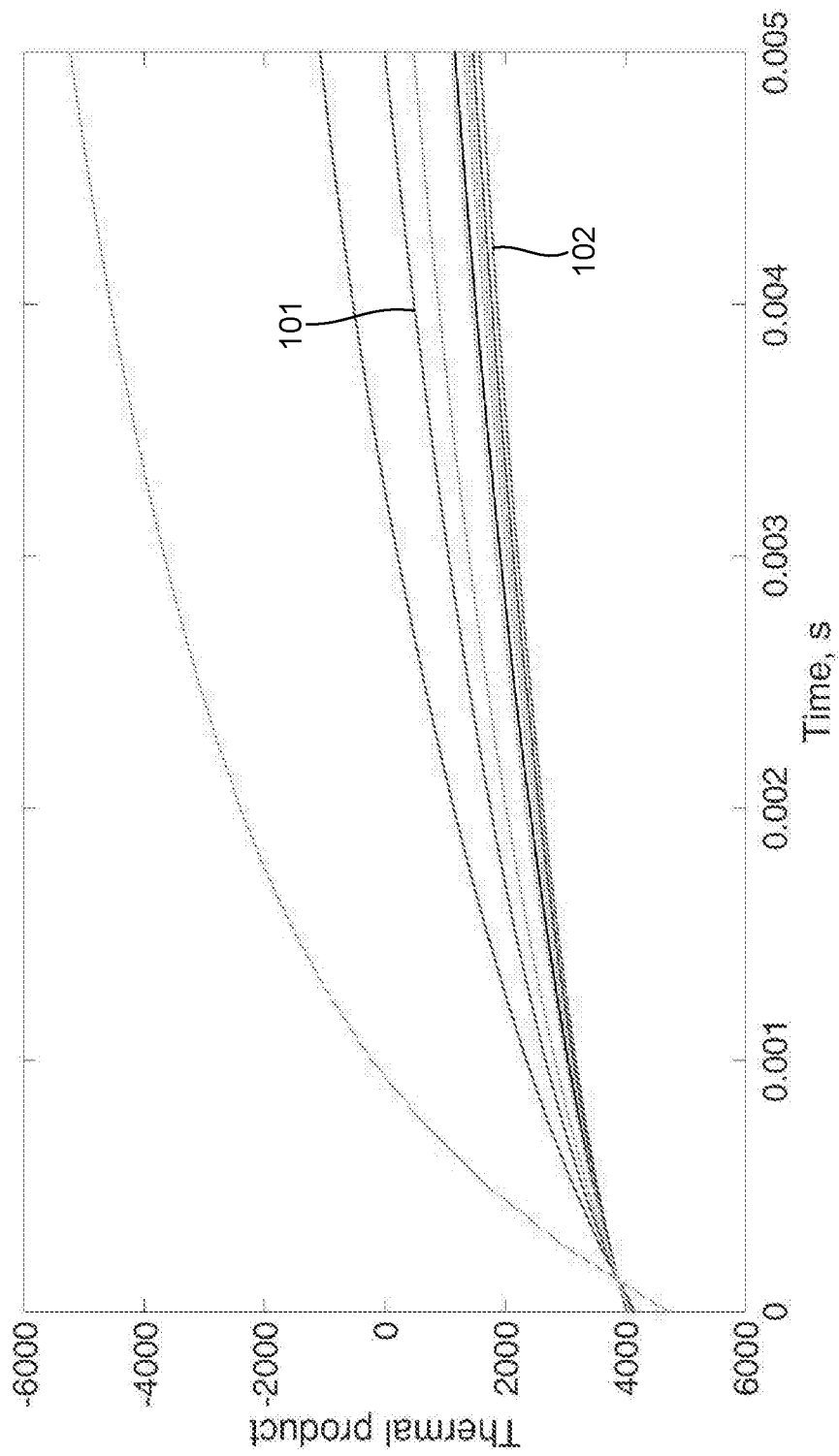
FIG. 15 is a graph showing a measured sensor element response during a heating pulse applied in 11 separate measurements, including nine measurements on different liquid medicines, and measurements on air and water for comparison.

FIG. 15 is a graph showing a measured sensor element response during a heat pulse applied in 11 separate measurements, including nine measurements on liquid medicines of different types (including cough medicine, paracetamol for older children, paracetamol for younger children, ibuprofen, anti-histamine, antacid, decongestant, and antibiotic), and measurements on air (101) and water (102). It can be seen that the different medicines can be distinguished from each other and from air and water. A particularly clear difference is seen for the antacid formulation (uppermost curve).

Figure 16:
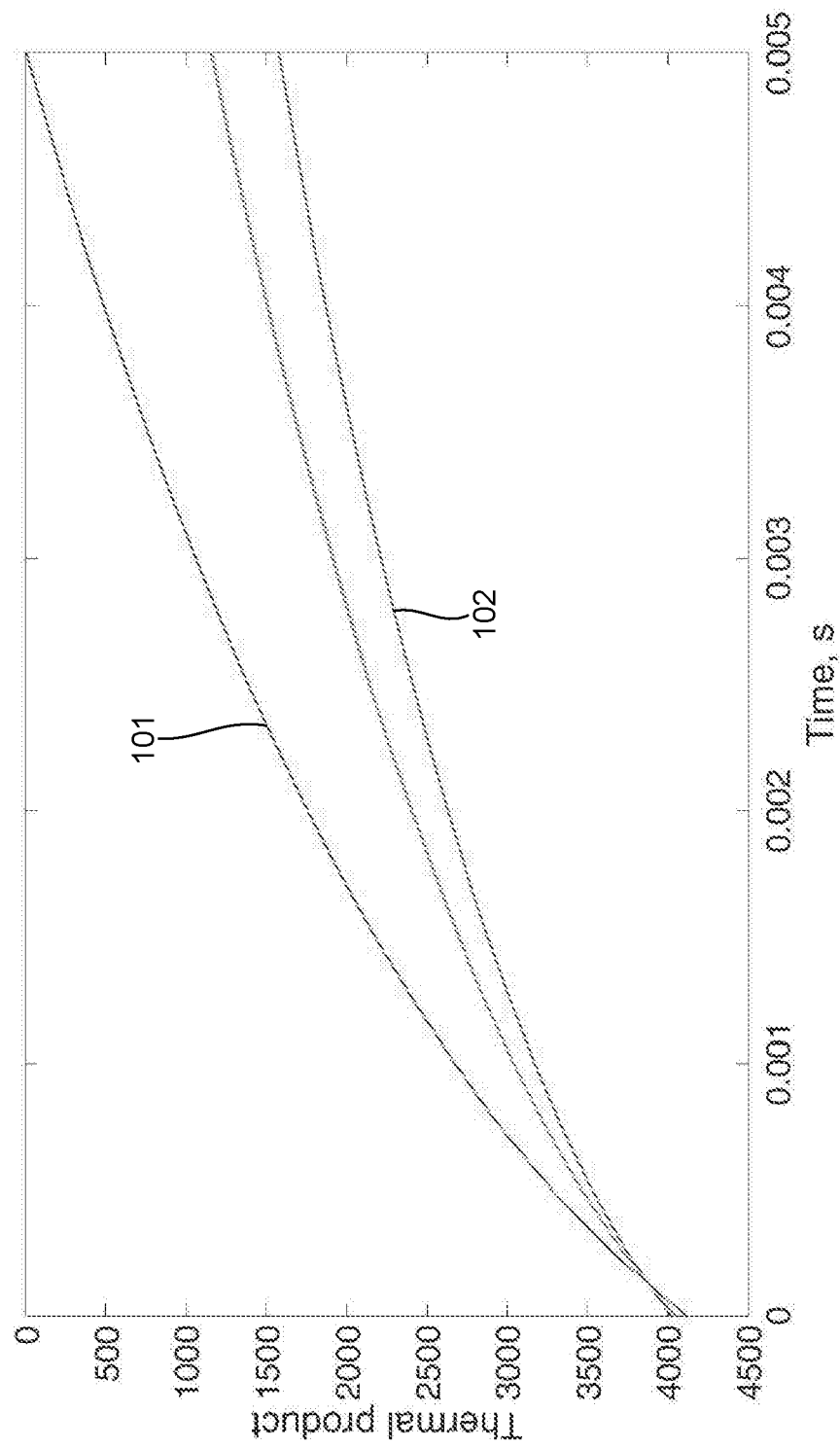
FIG. 16 is a graph showing a measured sensor element response during a heating pulse applied in four separate measurements, including measurements of the same liquid cough medicine from two different batches, and measurements on air and water for comparison.

FIG. 16 is a graph showing a measured sensor element response during a heating pulse applied in four separate measurements, including measurements of the same liquid cough medicine from two different batches, and measurements on air (101) and water (102). The two curves for the cough medicine lie almost exactly on top of each other and are very different from both air and water. This demonstrates the high degree of reproducibility of the method. Small deviations in the composition will be detected with high sensitivity.

Figure 17:
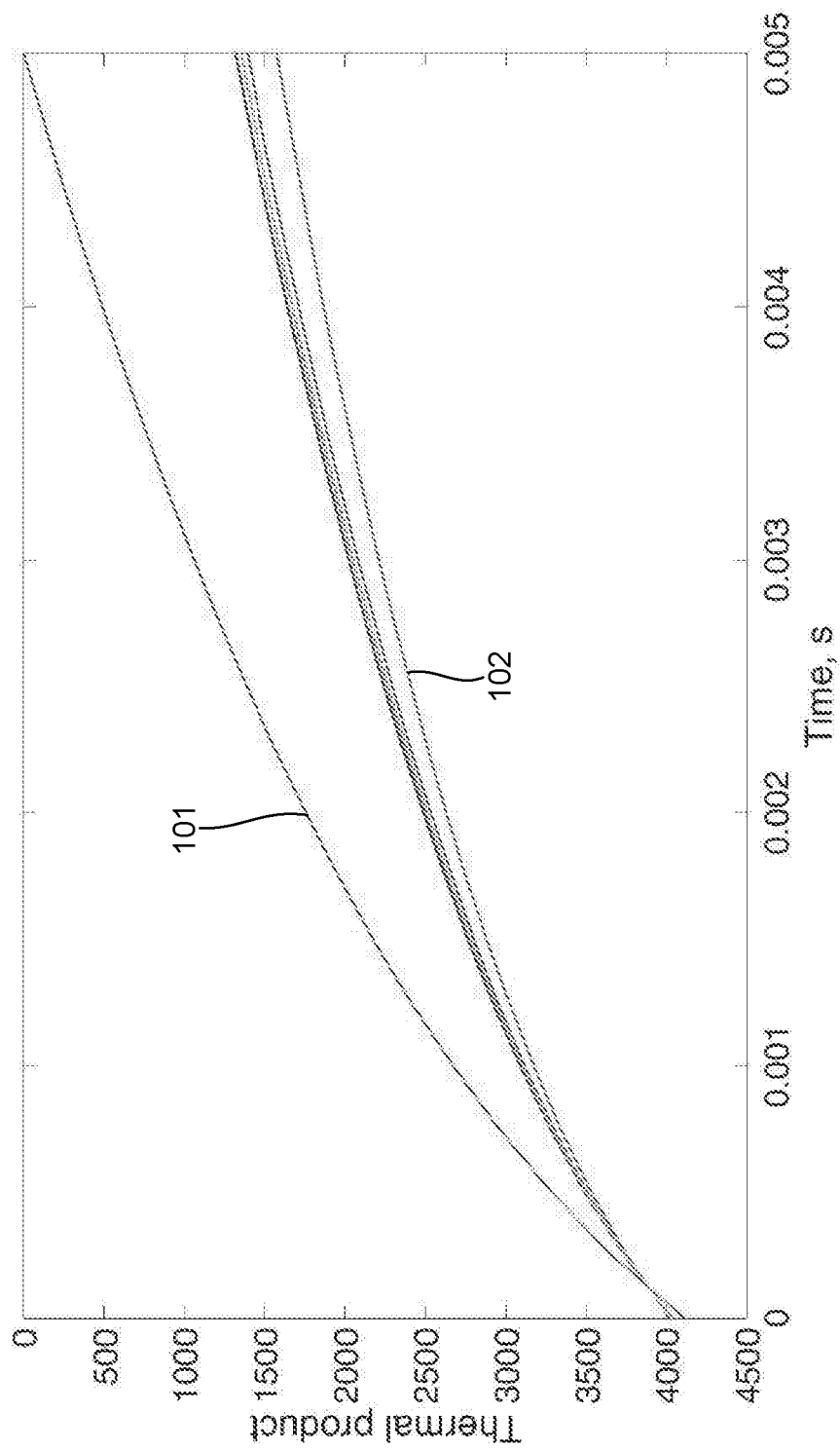
FIG. 17 is a graph showing a measured sensor element response during a heating pulse applied in seven separate measurements, including two measurements of a liquid paracetamol medicine for older children from different batches, three measurements of a liquid paracetamol medicine for younger children from different batches, and measurements on air and water for comparison.

FIG. 17 is a graph showing a measured sensor element response during a heating pulse applied in seven separate measurements, including two measurements of a liquid paracetamol medicine for older children from different batches, three measurements of a liquid paracetamol medicine for younger children from different batches, and measurements on air (101) and water (102). All of the curves for the paracetamol are very different from both air and water and lie close to each other. There is a small detectable variation between different batches and between the version for older children and the version for younger children. These results further reinforce the high reproducibility and sensitivity of the methodology.

Figure 18:
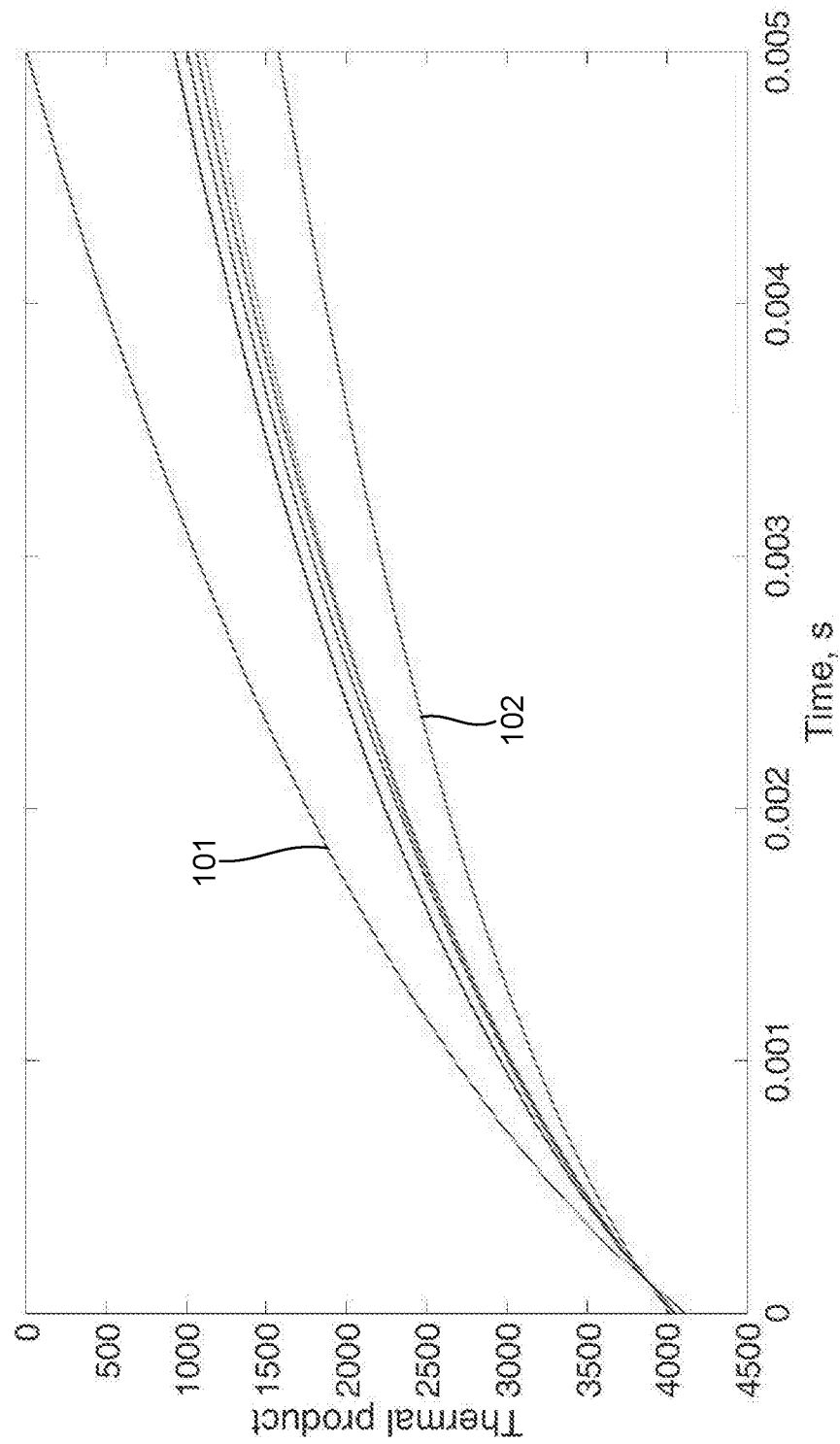
FIG. 18 is a graph showing a measured sensor element response during a heating pulse applied in six separate measurements, including four measurements of a liquid antibiotic medicine from different batches, and measurements on air and water for comparison.

FIG. 18 is a graph showing a measured sensor element response during a heating pulse applied in six separate measurements, including four measurements of a liquid antibiotic medicine from different batches, and measurements on air (101) and water (102). All of the curves for the antibiotic are very different from the curves for air and water. Furthermore, clear differences can be seen both between different batches and between different samples from the same batch. These results demonstrate the ability to detect small deviations in the composition of liquids being tested.

The invention claimed is:

1. A method of sensing a pharmaceutical product, comprising:
   using at least one sensor element to apply a first heating pulse and a second heating pulse to the pharmaceutical product; and determining chemical or structural information about the pharmaceutical product by measuring a first response of one of the at least one sensor element during the first heating pulse and a second response of one of the at least one sensor element during the second heating pulse, each response being dependent on a heat transfer characteristic of the pharmaceutical product, wherein:
   the information about the pharmaceutical product is at least partially obtained from a combination of the first measured response and the second measured response; and
   an average temperature of a region being sensed during obtaining of the first measured response is different from an average temperature of the region being sensed during obtaining of the second measured response.

2. The method of claim 1, wherein the pharmaceutical product comprises a solid body for oral administration, the solid body comprising a pharmaceutically active ingredient.

3. The method of claim 1, wherein the information obtained from the combination of the first measured response and the second measured response comprises information about the density of the pharmaceutical product.

4. The method of claim 1, wherein each sensor element comprises a resistive element and the responses of the sensor element comprises electrical responses of the resistive element.

5. The method of claim 1, wherein the pharmaceutical product comprises a liquid.

6. The method of claim 1, wherein the first and second heating pulses are applied via different sensor elements.

7. The method of claim 6, wherein the first and second heating pulses are applied during overlapping time periods.

8. The method of claim 1, wherein each sensor element comprises a resistive element and the heating pulses are applied by driving an electrical current through the resistive element.

9. The method of claim 8, wherein
each resistive element is mounted on a substrate in such a way that at least 10% of the surface area of the resistive element is in contact with the substrate via a support material encapsulating the resistive element.

10. The method of claim 8, wherein
each resistive element is mounted on a substrate in such a way that at least 10% of the surface area of the resistive element is in contact with the substrate.

11. The method of claim 10, wherein the resistive element is a thin film resistive element having a first surface configured to face towards the pharmaceutical product to be sensed and a second surface facing towards the substrate.

12. A method of sensing, comprising:
using at least one sensor element to apply a first heating pulse and a second heating pulse to a target material; and determining chemical or structural information about the target material by measuring a first response of one of the at least one sensor element during the first heating pulse and a second response of one of the at least one sensor element during the second heating pulse, each response being dependent on a heat transfer characteristic of the target material, wherein:
the information about the target material is at least partially obtained from a combination of the first measured response and the second measured response; and
an average temperature of a region being sensed during obtaining of the first measured response is different from an average temperature of the region being sensed during obtaining of the second measured response.

13. A method of sensing a pharmaceutical product, comprising:
using a sensor element to apply a heating pulse to the pharmaceutical product; and
determining chemical or structural information about the pharmaceutical product by measuring a response of the sensor element during the heating pulse, the response being dependent on a heat transfer characteristic of the pharmaceutical product, wherein:
the sensor element comprises a resistive element and the heating pulse is applied by driving an electrical current through the resistive element; and
wherein the resistive element is mounted on a substrate in such a way that at least 10% of the surface area of the resistive element is in contact with the substrate.

14. A method of sensing a pharmaceutical product, comprising:
using a sensor element to apply a heating pulse to the pharmaceutical product; and
determining chemical or structural information about the pharmaceutical product by measuring a response of the sensor element during the heating pulse, the response being dependent on a heat transfer characteristic of the pharmaceutical product,
wherein the pharmaceutical product comprises plural layers of different chemical or structural composition, heat from the heating pulse propagates through the plural layers, and the measured response of the sensor element is analysed to identify one or more target time periods, each target time period being defined as a time period in which the response of the sensor element is determined predominantly by a different combination of one or more of the plural layers.

* * * * *